United States Patent [19]
Jacobs et al.

[11] Patent Number: 5,824,338
[45] Date of Patent: Oct. 20, 1998

[54] CAPLET AND GELATIN COVERING THEREFOR

[75] Inventors: Richard L. Jacobs, Portage; Shirish A. Shah, Kalamazoo, both of Mich.

[73] Assignee: L. Perrigo Company, Allegan, Mich.

[21] Appl. No.: 699,450

[22] Filed: Aug. 19, 1996

[51] Int. Cl.⁶ .............................. A61K 9/64; A61K 9/48
[52] U.S. Cl. .................... 424/460; 424/451; 424/453; 424/456
[58] Field of Search ................... 424/451, 453, 424/456, 460

[56] References Cited

U.S. PATENT DOCUMENTS

| | | |
|---|---|---|
| 462,990 | 11/1891 | Oppenheimer . |
| 2,553,071 | 5/1951 | Van Sant . |
| 2,584,166 | 2/1952 | Stevenson et al. . |
| 4,478,596 | 10/1984 | Michelson . |
| 4,478,658 | 10/1984 | Wittwer . |
| 4,773,907 | 9/1988 | Urquhart et al. . |
| 4,792,451 | 12/1988 | Kim . |
| 4,820,524 | 4/1989 | Berta . |
| 4,867,983 | 9/1989 | Berta . |
| 4,883,182 | 11/1989 | Hughes . |
| 4,928,840 | 5/1990 | Barshay et al. . |
| 4,966,771 | 10/1990 | Berta . |
| 5,074,426 | 12/1991 | Goodhart et al. . |
| 5,089,270 | 2/1992 | Hampton et al. . |
| 5,146,730 | 9/1992 | Sadek et al. . |
| 5,213,738 | 5/1993 | Hampton et al. . |
| 5,314,696 | 5/1994 | Paulos . |
| 5,317,849 | 6/1994 | Sauter . |
| 5,415,868 | 5/1995 | Smith et al. . |
| 5,464,631 | 11/1995 | Hoover et al. . |

*Primary Examiner*—Carlos A. Azpuru
*Attorney, Agent, or Firm*—Price, Heneveld, Cooper, DeWitt & Litton

[57] ABSTRACT

A medicament includes a caplet having a peripheral land which is inserted into mating capsule shell halves each with internally formed recesses defining external peripheral lands which align when the shell halves are fitted over the caplet. In one embodiment of the invention, the internal diameter of the capsule shells is selected such that the caplet will fit within the capsule cell regardless of its orientation, while in another embodiment the caplet land mates with the internal recesses of the capsule shells. In a preferred embodiment of the invention, the capsule shells have different lengths and diameters such that one overlaps the other and can be sealed.

13 Claims, 2 Drawing Sheets

5,824,338

CAPLET AND GELATIN COVERING THEREFOR

BACKGROUND OF THE INVENTION

The present invention relates to a caplet shaped medicament and correspondingly shaped gelatin over therefor.

Capsules have long been recognized as a preferred form of medicament for the delivery of active ingredients, which may take the form of powder, liquid, granules or a solid encapsulated capsule-like medicament. In view of the tamperability of conventional capsules made with hard-shell capsule halves of different diameters which can be taken apart, steps have been taken, including the banding of capsule halves to reduce the possibility of tampering. Although sealing of capsule shell halves, commonly referred to as belly-banding, has proven effective to prevent tampering and make tampering evident to the consumer. Solid dosage forms, which are coated to improve swallowability with a gelatin or other coating, provide a gelcap dosage form which further reduces tamperability. U.S. Pat. Nos. 5,089,270; 5,213,738; 5,415,868; 4,820,524; 4,867,983; and 4,966,771 represent different approaches to providing a capsule-shaped product in the form of a caplet having a coating or covering which provides the appearance and, therefore, the consumer acceptability, of the popular capsule.

U.S. Pat. Nos. 5,415,868 and 5,317,849 disclose different manners by which either hard shell capsule halves can be shrink-wrapped onto a caplet ('868), or a caplet core covered at opposite ends with a soft gelatin capsule shell half which is subsequently dried to simulate a capsule-like medicament ('849). U.S. Pat. No. 5,464,631 suggests that studies have also shown the functional importance to consumers of providing a capsule-appearing solid dosage form which is multi-colored. The utilization of two colors can serve the function of identifying the type of medication, as well as providing a capsule-appearing product with a psychologically perceived medicinal efficacy. Aesthetically, also, consumers apparently prefer the attractive appearance of multi-colored capsules over single-colored capsules.

Thus, there has been an increase of activity by the pharmaceutical industry to provide over-the-counter caplet dosage forms which simulate the appearance of capsules and which have a variety of multiple colors which identify the type of medication provided so that the consumer can readily identify, for example, if the product is a particular type of analgesic or whether it includes antihistamines or other active ingredients in combination with analgesics. Such solid dosage forms have preferably been in the shape of a caplet and have been variously referred to as gelcaps or gel capsules and constitute solid caplet cores coated or covered with gelatin or other material. The above identified patents teach different approaches to providing the consumer with a capsule-appearing medicament; however, their manufacture requires either specialized manufacturing equipment or processes and tends to be somewhat expensive due to the manufacturing process. Also, when encapsulating a conventional, commercially available caplet which has sidewalls with conventional hard shell capsules, a uniform fit over the caplet cannot be achieved. U.S. patent application Ser. No. 08/606,647 filed on Feb. 26, 1996, and entitled "Multi-Colored Medicament" overcomes some of the difficulties encountered by the existing manufacturing process by providing a conventional caplet with a single-colored covering and subsequently providing a multi-colored appearance for the caplet by coloring one end thereof to provide a two-colored medicament.

SUMMARY OF THE PRESENT INVENTION

In order to improve upon the uniformity of covering of a conventional caplet which by nature of its formation includes a longitudinally extending outwardly projecting land around its periphery, an improved hard shell capsule is provided which accommodates the conventional caplet shape and encapsulates the caplet to provide a medicament which conforms in appearance to a coated caplet and eliminates the need for expensive machinery and processes.

In a preferred embodiment of the invention, a medicament is provided which includes a conventional caplet having a peripheral land which is inserted into mating capsule shell halves each with internally formed recesses conforming to the shape of the land. In one embodiment of the invention, the internal diameter of the capsule shells is selected such that the caplet will fit within the capsule shells regardless of the mating of the caplet land with the internal recess of the capsule shells. In another embodiment, the capsule shells are dimensioned for receiving the caplet land for providing a closely fitting capsule shell and caplet. In a preferred embodiment of the invention, the capsule shells have different lengths such that one overlaps the other and can be sealed for safety. The resultant medicament provides an easily swallowed caplet with a covering allowing an improved mating fit with the caplet and which can be manufactured at a reasonable cost.

These and other features, objects and advantages of the present invention will become apparent upon reading the following description thereof together with reference to the accompanying drawings.

DETAILED DESCRIPTION OF THE PREFERRED EMBODIMENT

Figure 1:
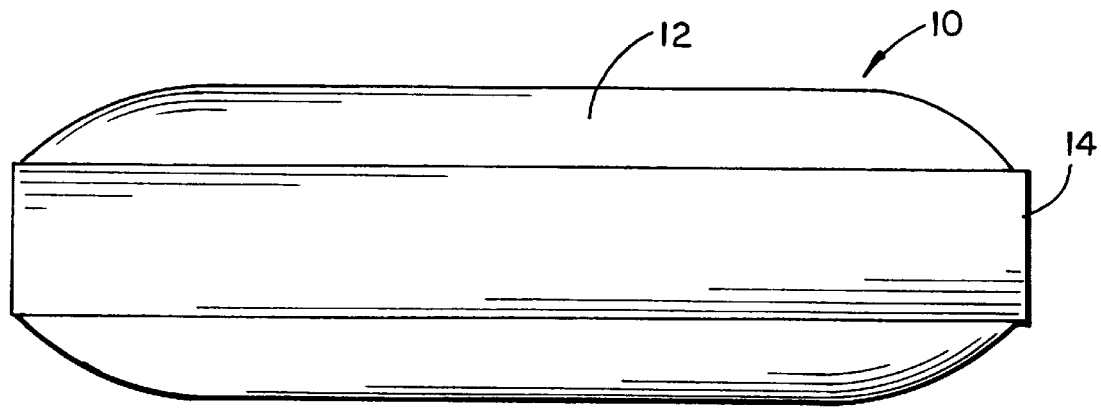
FIG. 1 is a side elevational view of a caplet.
Figure 2:
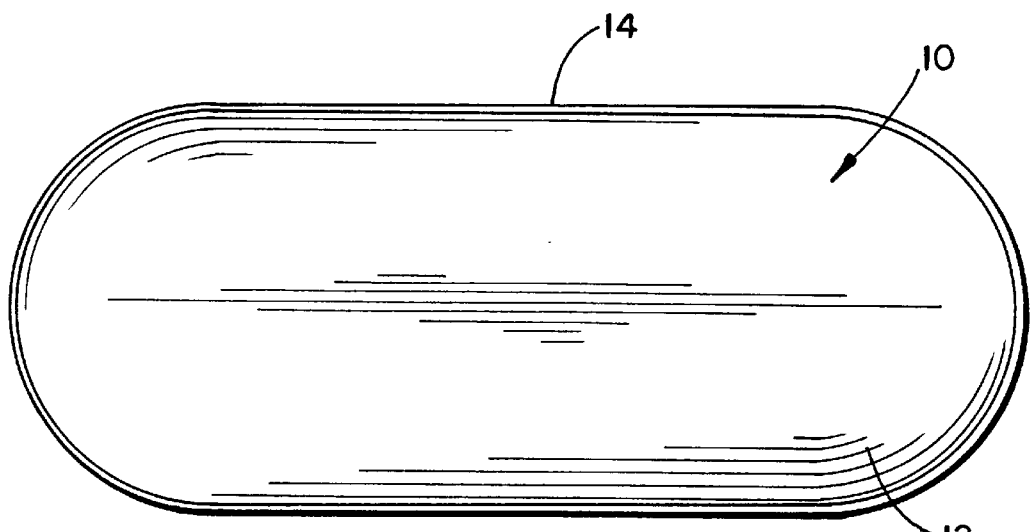
FIG. 2 is a top plan view of the caplet shown in FIG. 1.
Figure 3:
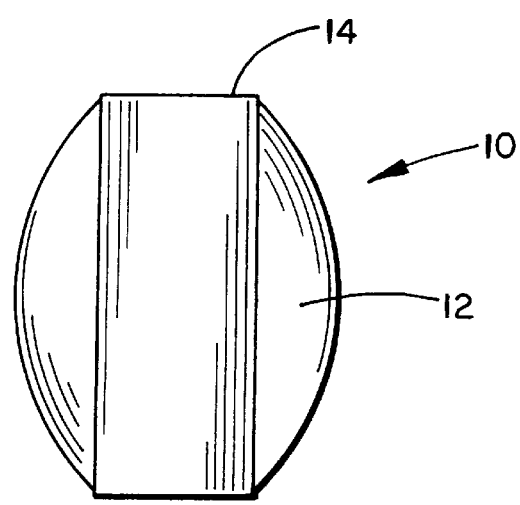
FIG. 3 is a right-side view of the caplet shown in FIG. 2.
Figure 4:
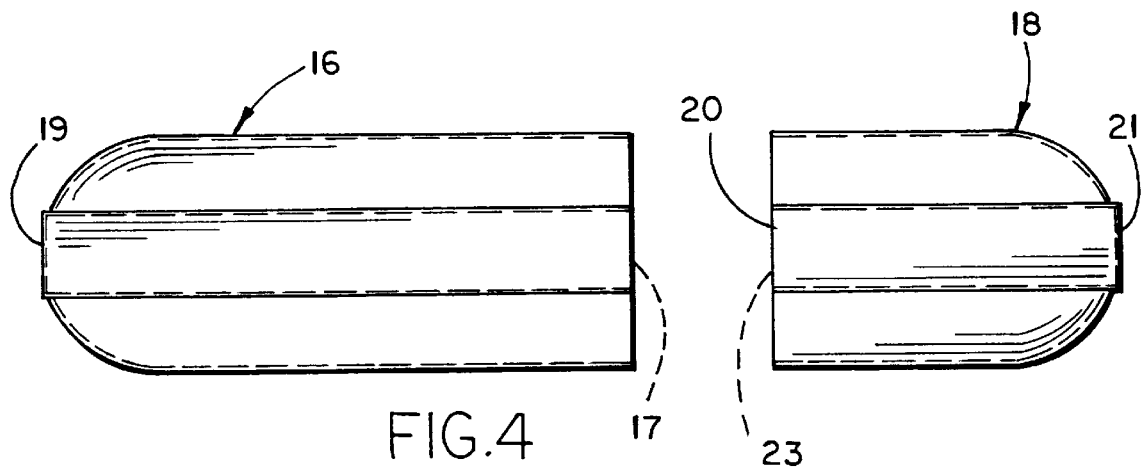
FIG. 4 is an exploded side elevational view of the capsule shells embodying the present invention.

Referring initially to FIGS. 1–3, there is shown a caplet 10 forming the core of a medicament 30 (FIG. 5) of the present invention. Caplet 10 is conventionally formed by pressing a blend of suitable active ingredients and excipients which may be either their natural color, including white, or can be conventionally colored as desired to provide a conventional, caplet-shaped core of any desired color. The active ingredients may be any analgesic such as acetylsalicylic acid, acetaminophen, ibuprofen or any other NSAID, which are commonly known and which can be pressed into the shape of a caplet utilizing conventional existing tableting equipment and processes. The caplet 10 may also exclusively include other active ingredients, such as antihistamines or a combination of analgesics and antihistamines, or other ingredients as is conventional. The caplet 10 includes a central body 12 having a generally elongated, somewhat oval shape, as seen in the top view of FIG. 2, and a horizontally extending peripheral land 14 extending around the central periphery of the caplet. This land is formed by the pressing process in conventional caplet-forming equipment where the caplet is pressed vertically, as seen in FIG. 1.

Typically, such caplets will be coated utilizing a dip or spray coating process for coating the caplet with any number of medicinally acceptable coverings such as gelatin, Opadry®, Providone®, methyl-cellulose, or other clear, film-forming materials which increase the swallowability of the caplet by providing a slippery covering to ease the physical swallowing process and also mask the taste of the ingredients which may be contained in the caplet. Instead of such a conventional coating, the caplet 10 of the present invention is encapsulated by the covering shown in FIGS. 4–7, which covering comprises first and second shells 16 and 18, with shell 16 having a length somewhat greater than the shell 18 and dimensioned to fit within the end 20 of shell 18. Shells 16 and 18 are made of a material which is dissolvable for exposing the caplet to the individual's digestive system and can be any medically suitable material with gelatin being preferred. Shell 16 includes a generally circular cross section having an internally formed recess 17 defining an externally extending land 19 conforming in appearance to land 14 of caplet 10. Capsule half 18 likewise has a generally circular cross section having an internal diameter slightly greater than the external diameter of capsule shell 16, and an internally extending recess 23 defining an outwardly extending land 21 conforming also to the general appearance of land 14 of caplet 10 shown in FIGS. 1–3.

Figure 5:
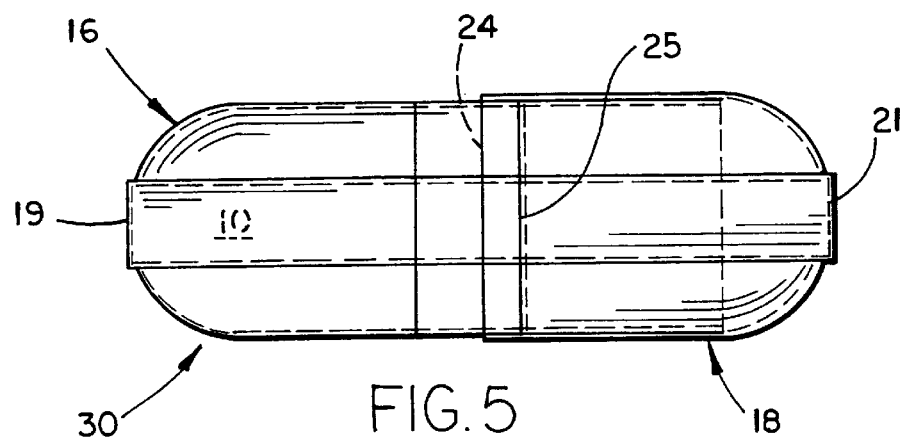
FIG. 5 is a side elevational view of an assembled medicament embodying the present invention.
Figure 6:
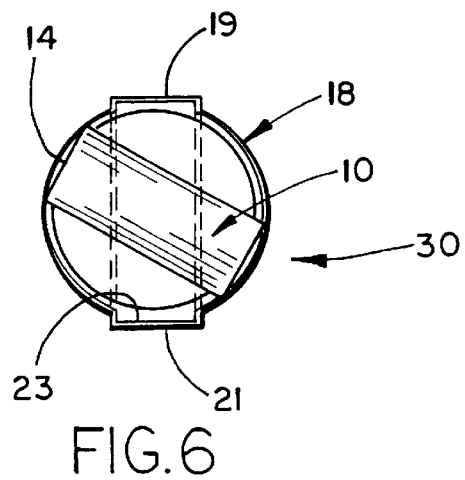
FIG. 6 is a vertical cross-sectional view of a medicament embodying the present invention showing a first orientation of the caplet within the capsule shells.

The capsule shells 16 and 18 are formed using conventional hard shell gelatin caplet forming equipment and processes, with the exception that the pins which are dip-coated with gelatin to form the caplet shells are shaped to define the outwardly extending lands 19 and 21 defining also the internal recesses 17 and 23, respectively. In the preferred embodiment, the covers or shells 16 and 18 overlap as seen in FIG. 5, although in other embodiments it may be desirable to have the capsule shells of equal diameter and butt-joined. To provide tamper resistance and evidence, a conventional gelatin band or seal 25 extends around the junction 24 of the completed medicament, as seen in FIG. 5, and seals the medicament. The internal diameter of the capsule cover 16 in the preferred embodiment is sufficient to allow the largest diameter portion of caplet 10 to orient itself within the capsule cover in any desired orientation, as seen in FIG. 6. Thus, the land 19 or 21 of the caplet cover 16 and 18, respectively, need not align with the land 14 of the caplet, as illustrated in FIG. 6. The resultant medicament tightly engages the edges of the caplet land 14 and has the swallowability of a coated caplet and a somewhat flatter appearance than a conventional capsule due to the lands 19 and 21 extending from the hard shell gelatin capsule halves 16 and 18.

Figure 7:
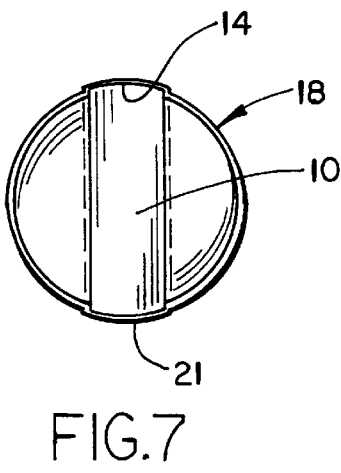
FIG. 7 is a vertical cross-sectional view through a medicament embodying the present invention showing an alternate alignment of the caplet and capsule shells.

The diameter of the capsule covers 16 and 18 can be selected to accommodate the caplet 10 in any orientation, as illustrated in FIG. 6, or if desired, can be selected such that the land 14 of the caplet 10 aligns with the internal recesses 17 and 23 of caplet covers 16 and 18, as seen in the cross section of FIG. 7. In this embodiment, it is necessary, however, to align the capsule covers 16 and 18 during assembly with the land 14 of the caplet. This can be accomplished with capsule loading equipment designed to orient the caplet 10 in predetermined relationship to each of the hard shell capsule covers 16 and 18, which are also aligned to overlap with the lands 19 and 21, overlapping and aligned as seen in FIG. 5.

Regardless of the orientation of the caplet in the capsule, the covers are shaped to include the longitudinally extending internal recess defining the external land having a height substantially the same or slightly greater than the height of the land 14 on a caplet. The gelatin employed for the covers 16 and 18 can be a clear gelatin or colored in matching or different colors to provide the desired appearance of the resultant medicament to identify the medication contained within the cover and to provide a pleasing aesthetic appearance to the medicament. In one embodiment of the invention, the caplet 10 was an acetaminophen caplet with a length of 0.753 inches, a height of 0.24 inches and a land height of 0.096 inches. Gelatin shell 16 had a length of 0.646 inches, an internal diameter of 0.253 inches, an outer diameter of 0.261 inches and a recess height of 0.096 inches. Shell 18 had a length of 0.38 inches, an internal diameter of 0.264 inches, an outer diameter of 0.272 inches and a land height of 0.1 inches, such that caplet 10 fits relatively tightly within shell 16 which, in turn, fits within shell 18.

Thus, the medicament of the present invention provides a two-piece gelatin covering for a conventional caplet which conforms to the shape of the caplet and which can be sealed to provide tamper resistance and tamper evident protection for the consumer while providing an easy-to-swallow medicament.

It will become apparent to those skilled in the art that various modifications to the preferred embodiment of the invention as defined by the appended claims can be made without departing from the spirit or scope thereof as defined by the appended claims.

The embodiments of the invention in which an exclusive property or privilege is claimed are defined as follows:

1. A medicament comprising:
    a solid caplet comprising a pressed mixture of excipients and active ingredients, said caplet including a generally elongated body having a peripheral land extending around the center line thereof, and
    a gelatin cover for said caplet comprising two dissolvable shells, each with a longitudinally extending peripheral recess defining an external land and wherein the internal diameter of each of said shells is selected to receive said caplet with said peripheral recesses of said shells aligned with and extending over said peripheral land of said caplet, wherein said shells are shaped to conform to the external surface of said caplet.

2. The medicament as defined in claim 1 wherein one of said shells has a length and diameter different than the other of said shells, such that said shells overlap when fitted together with said external lands aligned and overlapping.

3. The medicament as defined in claim 2 wherein said shells are made of gelatin.

4. The medicament as defined in claim 3 wherein the junction of said shells is sealed with a gelatinous material.

5. The medicament as defined in claim 4 wherein one of said shells has a color different than the other of said shells.

6. A medicament comprising:
    a solid caplet comprising a pressed mixture of excipients and active ingredients, said caplet including a generally oval body including a flat side defining an outwardly extending peripheral land extending around the center line thereof; and
    a gelatin cover for said caplet comprising a pair of mating dissolvable shells, each with an enclosed end and an open end, each of said shells further including a longitudinally extending peripheral recess defining an external land and wherein said shells are dimensioned to conform to the external surface of said caplet and receive said caplet with said land of said caplet extending into said peripheral recesses of said shells.

7. The medicament as defined in claim 6 wherein one of said shells has a length and diameter different than the other of said shells, such that said shells overlap when fitted together.

8. The medicament as defined in claim 7 wherein said shells are made of gelatin.

9. The medicament as defined in claim 8 wherein the junction of said shells is sealed with a gelatinous material.

10. The medicament as defined in claim 9 wherein one of said shells has a color different than the other of said shells.

11. The medicament as defined in claim 6 wherein said shells are made of gelatin.

12. The medicament as defined in claim 11 wherein the junction of said shells is sealed with a gelatinous material.

13. The medicament as defined in claim 12 wherein one of said shells has a color different than the other of said shells.

* * * * *